United States Patent [19]

Chang et al.

[11] Patent Number: 5,243,117

[45] Date of Patent: Sep. 7, 1993

[54] CATALYST AND PROCESS FOR THE SELECTIVE PRODUCTION OF PARA-DIALKYL SUBSTITUTED BENZENES

[75] Inventors: Clarence D. Chang, Princeton; David S. Shihabi, Pennington, both of N.J.

[73] Assignee: Mobil Oil Corp., Fairfax, Va.

[21] Appl. No.: 533,150

[22] Filed: Jun. 5, 1990

[51] Int. Cl.⁵ ............................ C07C 3/52; C07C 3/62
[52] U.S. Cl. .................................. 585/467; 585/475
[58] Field of Search ............ 585/471, 467, 468, 475; 502/71; 423/328, 328 C

[56] References Cited

U.S. PATENT DOCUMENTS

| | | | |
|---|---|---|---|
| 3,702,886 | 11/1972 | Argauer et al. | 423/328 |
| 4,090,981 | 5/1978 | Rodewald | 252/455 Z |
| 4,117,026 | 9/1978 | Haag et al. | 260/671 R |
| 4,127,616 | 11/1978 | Rodewald | 260/671 R |
| 4,175,114 | 11/1979 | Plank et al. | 423/329 |
| 4,175,144 | 11/1979 | Plank et al. | 423/329 |
| 4,199,556 | 4/1980 | Plank et al. | 423/329 |
| 4,341,748 | 7/1982 | Plank et al. | 423/328 |
| 4,465,886 | 8/1984 | Rodewald | 585/467 |
| 4,477,583 | 10/1984 | Rodewald | 502/71 |
| 4,752,596 | 6/1988 | Bergna et al. | 502/64 |

FOREIGN PATENT DOCUMENTS 0030811 6/1981 European Pat. Off.
0088158 9/1983 European Pat. Off.
0289691 9/1988 European Pat. Off.

Primary Examiner—Asok Pal
Assistant Examiner—P. Achutamurthy
Attorney, Agent, or Firm—Alexander J. McKillop; Dennis P. Santini

[57] ABSTRACT

A silicon-modified non-organic zeolite catalyst and a process for the selective production of para-dialkyl substituted benzenes using the silicon-modified non-organic high alumina zeolite.

20 Claims, 1 Drawing Sheet

FIG. IA
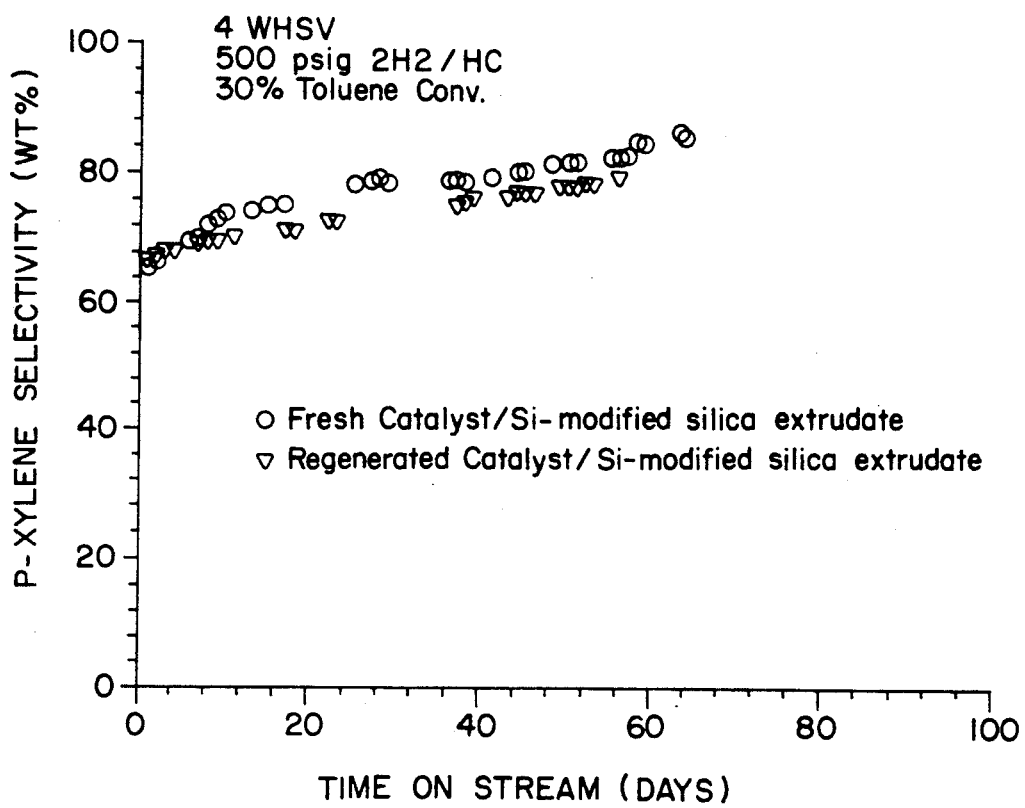
FIG. IB
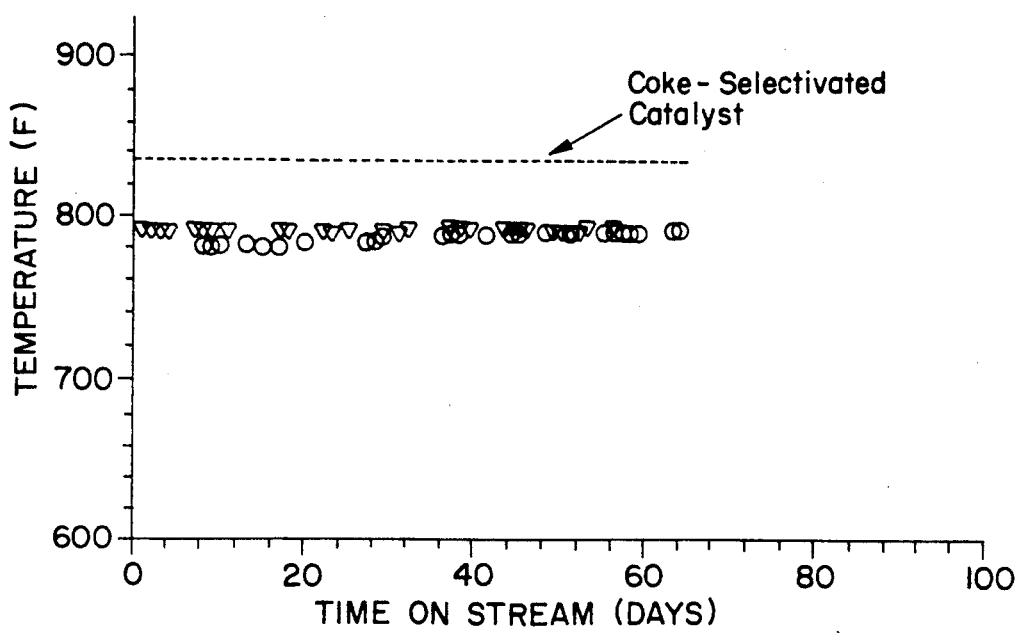

CATALYST AND PROCESS FOR THE SELECTIVE PRODUCTION OF PARA-DIALKYL SUBSTITUTED BENZENES

BACKGROUND OF THE INVENTION

The present invention is directed to a catalyst and a process for the selective production of para-dialkyl substituted benzenes, and particularly, an improved catalyst and a process for the selective production of para-dialkyl substituted benzenes using a silica-modified catalyst.

Processes for the selective production of para-dialkyl substituted benzenes are known in the art. For example, U.S. Pat. No. 4,090,981 to Rodewald discloses a method for making a catalyst particularly suitable for the selective production of para-dialkyl substituted benzenes wherein a porous crystalline aluminosilicate zeolite is coated with a silica and then subject to heating in an oxygen containing atmosphere at temperatures in excess of 300° C. U.S. Pat. No. 4,117,026 to Haag et al. discloses the production of dialkylbenzenes by the disproportionation of monoalkylbenzenes over zeolites pretreated with difficultly reducible oxides, including magnesium oxide, or coke. U.S. Pat. No. 4,127,616 to Rodewald discloses a process wherein a monoalkyl-substituted benzene having 1–4 carbon atoms and a mixture of benzene with an alkylating agent containing 1–4 carbon atoms is mixed with a zeolite having a silica coating. U.S. Pat. No. 4,465,886 to Rodewald also discloses a silica-modified catalyst for use in the selective production of paradialkyl substituted benzenes. U.S. Pat. No. 4,477,583 to Rodewald relates to a method of preparing a composition having a crystalline zeolite with a coating of silica which is useful in the selective production of para-dialkyl substituted benzenes. These patents contemplate the use of zeolite catalysts synthesized in the presence of organonitrogen templates. Such catalysts, hereinafter referred to as "organic catalysts", are disclosed in U.S. Pat. No. 3,702,886 to Argauer et al.

SUMMARY OF THE INVENTION

The present invention is directed to a silica modified non-organic catalyst and an improved process for the selective production of para-dialkyl substituted benzenes utilizing the silica modified non-organic catalyst. The present invention provides greater para-selectivity for a given conversion than the processes of the prior art. The process of the present invention is also useful in obtaining para-dialkyl substituted benzenes in high selectivity at lower temperatures than previously available using processes known in the art.

BRIEF DESCRIPTION OF THE DRAWINGS

FIGS. 1A and 1B are graphic representations of the p-xylene selectivity at time and temperature of regenerated and fresh catalyst, respectively, of the present invention as compared to the prior art coke-selectivated catalysts.

DETAILED DESCRIPTION

The present invention achieves an unexpected selectivity in the formation of para-dialkyl substituted aromatics by utilizing a non-organic, high aluminum zeolite with a silica binder. The non-organic, high aluminum zeolites contemplated by the present invention include those disclosed in U.S. Pat. Nos. 4,175,114 issued Nov. 20, 1979, 4,199,556 issued Apr. 22, 1980, and 4,341,748 issued Jul. 27, 1982 to Plank, et al. and co-pending U.S. Pat. application Ser. No. 317,735 filed Nov. 3, 1981, which are hereby incorporated by reference. By the term "high aluminum", it is meant that the silica to alumina ($SiO_2/Al_2O_3$) ratio is below about 30 and is preferably about 26. The process of the present invention can be successfully carried out using non-organic, high aluminum HZSM-5 which has been modified by treatment with an organosilicon compound, for example phenylmethylsilicone. The silicone modification can be accomplished by dissolving the organosilicon compound in an organic solvent, adding the zeolite, then heating the mixture to the solvent's boiling point to remove the solvent, and calcining the residue. Alternatively, the zeolite can be added to an aqueous emulsion of the organosilicon compound, and then the water can be evaporated.

The present invention is suitable for the alkylation of benzene or substituted benzene compounds, as well as the disproportionation of substituted benzene compounds. The present invention is particularly suitable for the selective disproportionation of toluene to p-xylene. The process of the present invention may be practiced over a range of reaction conditions such as at temperatures of about 500° F. to about 1200° F., and preferably about 600° F. to about 900° F., at pressures of about 200 psig to about 1000 psig, and preferably about 400 psig to about 800 psig, and at a weight hourly space velocity (WHSV) of about ½ to about 20 and preferably about 4 to about 10. The weight hourly space velocity is the weight of liquid flowing through the reactor every hour divided by the weight of zeolite in the catalyst.

One embodiment of the present invention comprises a process for the selective production of para dialkyl substituted benzenes wherein the alkyl group contains from 1 to 4 carbon atoms which comprises contacting, under conversion conditions, a hydrocarbon precursor selected from the group consisting of mono alkyl-substituted benzenes having 1–4 carbon atoms in the alkyl substituent and a mixture of said precursor or benzene with an alkylating agent containing from 1 to 4 carbon atoms with a non-organic catalyst comprising a porous crystalline aluminosilicate zeolite having deposited thereon a coating of silica which extensively covers and resides substantially exclusively on the external surface thereof as a result of contact with a silicone compound of a molecular size incapable of entering the pores of the zeolite and subsequent heating in an oxygen-containing atmosphere to a temperature in excess of 300° C. but below a temperature at which crystallinity of the zeolite is adversely affected at a rate such that the silicone compound does not volatilize prior to undergoing oxidation to silica, said zeolite being characterized by an activity, in terms of alpha value, of between about 2 and about 5000, a xylene sorption capacity greater than 1 gram/100 grams of zeolite and an ortho-xylene sorption time for 30 percent of said capacity greater than 10 minutes, said sorption capacity and sorption time being measured at 120° C. and a pressure of 4.5±0.8 mm. of mercury and recovering from the resulting product mixture, a para dialkyl substituted benzene in an amount greater than the thermodynamic equilibrium concentration thereof in the total dialkyl substituted benzenes produced.

The catalysts used in the present invention are advantageously stable and regenerable. The catalysts used in the present invention are also permanently "selectivated" and operate at lower temperatures leading to improved process operation and economics. In contrast, coke-selectivated catalysts, such as those disclosed in U.S. Pat. No. 4,117,026, require pre-coking after each regeneration cycle.

The following examples illustrate the advantages of the present invention:

EXAMPLE 1

An organic ZSM-5 zeolite was prepared according to U.S. Pat. No. 3,702,886, using tetrapropylammonium bromide template. The ZSM-5 product analysis showed $SiO_2/Al_2O_3 = 25.4$ molar ratio. This zeolite was silica-extruded to form an extrudate having 65 wt % ZSM-5 and 35 wt % silica. The extrudate was calcined in nitrogen at 1000° F. for 5-6 hrs. and then ion exchanged with 1N $NH_3NO_3$ at room temperature overnight, dried at 266° F., and calcined in air, raising the furnace temperature 2 degrees F./min. to 1000° F., and holding at this temperature 5-6 hrs., thus converting the zeolite component into the hydrogen form. To 0.6 grams of phenylmethylsilicone (molecular weight ca. 1686) dissolved in 20 cc of hexane was added 2.5 grams of this extrudate. The mixture was heated to 68° F. to remove hexane solvent, and the residue calcined in air by raising the temperature 2 degrees F./min to 1000° F. and holding at this temperature for 7 hours. The product was a silica-coated catalyst containing 10 wt % modifier silica.

EXAMPLE 2

A non-organic ZSM-5 zeolite was prepared according to U.S. Pat. No. 4,175,114. The ZSM-5 product analysis showed $SiO_2/Al_2O_3 = 26$ mole ratio. This zeolite was silica-extruded, converted to the hydrogen form, and treated with silicone in a manner identical to Example 1.

EXAMPLE 3

A catalyst was prepared according to Example 2 with the exception that extrusion was effected using alumina in place of silica. The finished catalyst contained 10 wt % modifier silica.

EXAMPLE 4

A catalyst was prepared according to Example 3 with the exception that double the amount of phenylmethylsilicone was utilized, yielding a finished catalyst containing 20 wt % modifier silica.

EXAMPLE 5

A catalyst was prepared according to Example 2 with the exception that dimethylsilicone (molecular weight 4835, 0.4 g. in 20 cc. hexane per 2.5 g. extrudate) was used in place of phenylmethylsilicone, yielding a finished catalyst containing 10 wt % modifier silica.

Toluene disproportionation activity of each of the catalysts was tested in a micro-unit. In each run, 2 to 2.3 grams of the 1/16" extrudate catalyst were mixed with 4–5 grams of sand. The mixtures were then charged to ⅜" o.d. stainless steel reactors and the runs performed under conditions of ≈600 psig, 4–8 WHSV (zeolite), $2H_2/HC$, and 685°–900° F. The toluene used was purified by percolating through activated alumina. Liquid and gas products were analyzed by G.C.

Table 1 contains results of toluene disproportionation using the organic zeolite catalyst of Example 1. It is evident that over a range of reaction conditions the p-xylene selectivity is close to equilibrium. Table 2 contains results of selective toluene disproportionation (STDP) over the silica-bound, silicone-modified non-organic catalysts of the instant invention (Example 2 and Example 5). Included for comparison are results obtained using an unmodified silica-bound non-organic catalyst. It is clear that the silicone-modified catalysts gave vastly superior results, affording xylene paraselectivities far in excess of equilibrium. Table 3 contains results of STDP over alumina-bound, silicone-modified non-organic catalysts of the present invention (Examples 3 and 4). Included for comparison are results obtained using an unmodified alumina-bound, non-organic catalyst. These results demonstrate that compared to silica-bound catalyst, higher loadings of modifier silica are necessary to achieve high xylene paraselectivity.

TABLE 1

SELECTIVE TOLUENE DISPROPORTIONATION OVER ORGANIC CATALYST

| Catalyst Modification | Example 1 Phenylmethysilicone | | | | | |
|---|---|---|---|---|---|---|
| Days on Stream | 03 | 05 | 06 | 11 | 12 | 13 |
| WHSV | 2.2 | 4.0 | 4.0 | 4.0 | 4.0 | 4.0 |
| $H_2/HC$ (mole) | 2/1 | 2/1 | 2/1 | 2/1 | 2/1 | 2/1 |
| Temperature (F.) | 739 | 831 | 878 | 880 | 900 | 900 |
| Pressure (psig) | 500 | 500 | 500 | 500 | 500 | 500 |
| Conversion (wt %) | 7.4 | 19.0 | 31.7 | 26.1 | 31.3 | 30.9 |
| Liquid Yield (wt %) | 100 | 99.6 | 99.1 | 99.6 | 98.6 | 98.6 |
| Benzene/Xylenes | 1.04 | 1.08 | 1.11 | 1.06 | 1.11 | 1.11 |
| Benzene Selec (%) | 40.9 | 42.3 | 42.0 | 41.1 | 41.5 | 41.4 |
| Xylenes Selec (%) | 53.3 | 53.2 | 51.5 | 52.7 | 50.8 | 50.7 |
| $C_5-$ | 0.00 | 0.06 | 0.26 | 0.11 | 0.53 | 0.54 |
| Benzene | 3.02 | 8.03 | 13.32 | 10.74 | 12.98 | 12.79 |
| Ethylbenzene | 0.00 | 0.06 | 0.22 | 0.17 | 0.26 | 0.26 |
| p-Xylene | 0.97 | 2.57 | 4.11 | 3.50 | 4.02 | 3.96 |
| m-Xylene | 2.02 | 5.10 | 8.20 | 7.00 | 8.07 | 7.06 |
| o-Xylene | 0.94 | 2.34 | 3.92 | 3.26 | 3.81 | 3.75 |
| $C_9+$ | 0.43 | 0.74 | 1.58 | 1.32 | 1.64 | 1.62 |
| Total Xylenes | 3.93 | 10.10 | 16.32 | 13.76 | 15.90 | 15.67 |
| p-Xylene selectivity, % | 24.6 | 25.4 | 25.2 | 25.4 | 25.3 | 25.3 |
| Theoretical Equilibrium | 23.6 | 23.4 | 23.3 | 23.3 | 23.2 | 23.2 |

TABLE 2

SELECTIVE TOLUENE DISPROPORTIONATION OVER SILICA-BOUND NON-ORGANIC CATALYSTS

| | Unmodified | | | Modified | | | | | | |
|---|---|---|---|---|---|---|---|---|---|---|
| | | | | Example 2 | | | | Example 5 | | |
| Catalyst Modification | Silica-Bound ZSM-5 None | | | Phenylmethyl-silicone | | | | Dimethyl-silicone | | |
| Days on Stream | 1 | 2 | 91 | 1 | 3 | 17 | 63 | 2 | 3 | 9 |
| WHSV | 4 | 6 | 8 | 4 | 4 | 7 | 7 | 6 | 6 | 6 |
| Temperature °F. | 739 | 739 | 760 | 739 | 739 | 781 | 792 | 808 | 826 | 822 |
| Toluene Conv., wt % | 34.5 | 26.2 | 30.9 | 30.4 | 30 | 29.5 | 30 | 27.5 | 33.1 | 28.6 |
| Yields. wt % | | | | | | | | | | |

TABLE 2-continued
SELECTIVE TOLUENE DISPROPORTIONATION OVER SILICA-BOUND NON-ORGANIC CATALYSTS

| | Unmodified | | | Modified | | | | | | |
|---|---|---|---|---|---|---|---|---|---|---|
| | Silica-Bound ZSM-5 | | | Example 2 Phenylmethylsilicone | | | | Example 5 Dimethylsilicone | | |
| Catalyst Modification | None | | | | | | | | | |
| C$_5$− | 1.0 | 0.5 | 0.3 | 1.7 | 1.3 | 0.9 | 1.1 | 0.4 | 1.4 | 0.7 |
| Xylenes | 17.5 | 13.7 | 17.0 | 14.9 | 14.6 | 14.5 | 15.0 | 14.6 | 16.7 | 14.8 |
| C$_9$+ | 1.4 | 1.0 | 0.7 | 0.4 | 0.5 | 0.5 | 0.5 | 0.8 | 1.2 | 0.9 |
| p-Xylene | 24.9 | 25.1 | 26.1 | 65.6 | 67.9 | 75.5 | 86.0 | 58.0 | 54.1 | 56.9 |
| Theoretical Equilibrium | 23.6 | 23.6 | 23.5 | 23.6 | 23.6 | 23.5 | 23.4 | 23.4 | 23.4 | 23.4 |

TABLE 3
SELECTIVE TOLUENE DISPROPORTIONATION OVER ALUMINA-BOUND NON-ORGANIC CATALYSTS

| | Unmodified | Modified | | | |
|---|---|---|---|---|---|
| | Alumina-Bound ZSM-5 | Example 3 Phenylmethylsilicone (10% modifier silica) | | Example 4 Phenylmethylsilicone (20% modifier silica) | |
| Catalyst Modification | None | | | | |
| Days on Stream | 2 | 2 | 15 | 2 | 3 |
| WHSV | 4 | 4 | 7 | 4 | 4 |
| Temperature °F. | 685 | 754 | 795 | 740 | 779 |
| Toluene Conv., wt % | 28.0 | 30.3 | 30.2 | 21.0 | 32.0 |
| Yields, wt % | | | | | |
| C$_5$− | 0.4 | 0.6 | 0.5 | 0.3 | 0.3 |
| Xylenes | 14.9 | 15.6 | 16.1 | 11.2 | 17.2 |
| C$_9$+ | 0.9 | 1.0 | 1.0 | 0.4 | 0.7 |
| P-Xylene selectivity | 24 | 27.6 | 29.1 | 54 | 49 |
| Theoretical Equilibrium | 23.7 | 23.5 | 23.5 | 23.6 | 23.5 |

EXAMPLE 6

The activity, p-xylene selectivity, aging characteristics, and regenerability of the catalyst of Example 2 are shown in FIG. 1 and Table 4. In this experiment, the first cycle was arbitrarily terminated after 63 days on stream, although the catalyst was still fully active, in order to demonstrate its regenerability. The catalyst was regenerated by calcination in air. The temperature was increased 2 F./min to 1000° F. and held for 4 hrs. As seen in FIG. 1 and Table 4, the catalytic performance of the regenerated catalyst substantially reproduces that of the fresh catalyst. It is further evident from FIG. 1, that the catalyst of the instant invention has a dramatic activity advantage over the coke-selectivated catalysts of the prior art. Table 5 compares selectivities achieved using the instant catalyst with typical results of a coke-selectivated ZSM-5.

TABLE 4
SELECTIVE TOLUENE DISPROPORTIONATION OVER FRESH VS. REGENERATED SILICA-BOUND ORGANIC CATALYSTS

| Catalyst | Fresh | | Regenerated | |
|---|---|---|---|---|
| Days on Stream | 8 | 17 | 8 | 17 |
| WHSV | 7 | 7 | 7 | 7 |
| Temperature °F. | 781 | 781 | 790 | 790 |
| Toluene Conv., wt % | 30.0 | 29.5 | 31.0 | 30.4 |
| Yields, wt % | | | | |
| C$_5$− | 1.3 | 0.9 | 1.3 | 1.5 |
| Xylenes | 14.3 | 14.5 | 14.7 | 15.4 |
| C$_9$+ | 0.4 | 0.5 | 0.8 | 0.8 |
| p-Xylene selectivity | 72.1 | 75.5 | 69.1 | 71.7 |

TABLE 5
SELECTIVE TOLUENE DISPROPORTIONATION
500 psig
4 WHSV
2 H2/HC
30% Toluene conversion

| | CATALYST | |
|---|---|---|
| | Coke-selectivated | Si-modified |
| Temperature, F. | 835 | 792* |
| C$_5$− | 1.7 | 1.1 |
| Benzene | 14.0 | 12.7 |
| p-Xylene | 12.6 | 12.9 |
| m-Xylene | 2.0 | 1.8 |
| o-Xylene | 0.2 | 0.3 |
| C$_9$+ | 0.4 | 0.5 |
| p-Selectivity | 85 | 86 |

*63 days on stream

EXAMPLE 7

A non-organic ZSM-5 zeolite prepared according to U.S. Pat. No. 4,175,114, is silica-extruded, and converted to the hydrogen form in a manner identical to Example 1. This is mixed with a 9% aqueous emulsion of phenylmethylsilicone to yield, after removal of water and calcination at 1000° F., a catalyst containing 9 wt % modifier silica. The catalyst is used for toluene disproportionation, giving 85% p-xylene selectivity at 790° F. and 30% conversion.

While the present invention is preferably practiced with non-organic, high alumina ZSM-5 zeolite such as those disclosed in the above-referenced patents and co-pending patent application, other shape-selective, non-organic zeolites may be used. As used herein, the term "non-organic" is used to mean the types of zeolites disclosed in the above-referenced patents and patent application to Plank, et al. having no or a limited amount of organic material present during formation.

We claim:

1. A process for the production of para-dialkyl substituted benzenes comprising the steps of:
   combining a non-organic zeolite with an organosilicon compound in forming a modified catalyst;
   contacting under conversion conditions said modified catalyst with at least one organic material selected from the group consisting of a) a substituted aromatic, and b) a mixture of benzene and at least one alkylating agent having 1–4 carbon atoms.

2. A process according to claim 1 wherein said organosilicon compound comprises phenylmethylsilicone.

3. A process according to claim 2 wherein said organic material comprises toluene.

4. A process according to claim 1 wherein said organosilicon compound comprises dimethylsilicone.

5. A process according to claim 4 wherein said organic material comprises toluene.

6. A process according to claim 1 wherein said non-organic zeolite and said organosilicon compound are calcined to form said modified catalyst.

7. A process according to claim 1 wherein said organic material comprises benzene and at least one alkylating agent having 1–4 carbon atoms.

8. A process according to claim 1 wherein said zeolite catalyst is a silica-bound zeolite.

9. A process according to claim 1 wherein said zeolite catalyst is a alumina-bound zeolite.

10. A process for the selective production of paradialkyl substituted benzenes having a conversion of at least about 10% and a para-selectivity of at least about 30% comprising the step of:
    contacting, under conversion conditions an organic material with a silicon-modified non-organic zeolite catalyst, wherein said organic material is selected from the group consisting of a) a alkyl-substituted benzene compounds, and b) a mixture of benzene and at least one alkylating agent.

11. A process according to claim 9 wherein said organic material comprises toluene.

12. A process according to claim 10 wherein said organic material comprises benzene and at least one alkylating agent having 1–4 carbon atoms.

13. A process according to claim 10 wherein said non-organic zeolite is modified with phenylmethylsilicone.

14. A process according to claim 10 wherein said non-organic zeolite is modified with dimethylsilicone.

15. A process according to claim 10 wherein said organic material and said zeolite are contacted at a temperature of below about 800° F.

16. A process according to claim 10 wherein said zeolite catalyst is a silica-bound zeolite.

17. A process for the selective production of para dialkyl substituted benzenes wherein the alkyl group contains from 1 to 4 carbon atoms which comprises contacting, under conversion conditions, a hydrocarbon precursor selected from the group consisting of mono alkyl-substituted benzenes having 1–4 carbon atoms in the alkyl substituent and a mixture of said precursor or benzene with an alkylating agent containing from 1 to 4 carbon atoms with a silica-modified non-organic zeolite catalyst.

18. A process according to claim 17 wherein said hydrocarbon precursor comprises toluene.

19. A process according to claim 17 wherein said catalyst comprises ZSM-5.

20. A process according to claim 17 wherein toluene is disproportionated.

* * * * *